United States Patent

Plaum et al.

[11] Patent Number: 5,859,241
[45] Date of Patent: Jan. 12, 1999

[54] PROCESS FOR THE PREPARATION OF A BENZOTHIAZEPINE

[75] Inventors: Marcus J. M. Plaum; Wilhelmus H. J. Boesten, both of Sittard, Netherlands

[73] Assignee: DSM N.V., Geleen, Netherlands

[21] Appl. No.: 821,519

[22] Filed: Mar. 21, 1997

[30] Foreign Application Priority Data

Mar. 22, 1996 [NL] Netherlands ............ 1002687

[51] Int. Cl.⁶ .................................... C07D 281/10
[52] U.S. Cl. ........................................ 540/591
[58] Field of Search ............................ 540/591

[56] References Cited

U.S. PATENT DOCUMENTS

| Re. 34,935 | 5/1995 | Rossey | 540/491 |
|---|---|---|---|
| 3,562,257 | 2/1971 | Kugita et al. | 540/591 |
| 5,013,835 | 5/1991 | Rossey | 540/491 |
| 5,102,998 | 4/1992 | Rossey | 540/491 |
| 5,128,469 | 7/1992 | Nishimoto | 540/491 |
| 5,294,706 | 3/1994 | Koumoto | 540/491 |

FOREIGN PATENT DOCUMENTS

| 378455-AI | 7/1990 | European Pat. Off. |
|---|---|---|
| 395302-A1 | 10/1990 | European Pat. Off. |
| 395323-A1 | 10/1990 | European Pat. Off. |
| 447135-A1 | 9/1991 | European Pat. Off. |
| A-57-122 065 | 7/1982 | Japan . |

Primary Examiner—Mark L. Berch
Attorney, Agent, or Firm—Pillsbury Madison & Sutro LLP

[57] ABSTRACT

Process for the preparation of a 1,5-benzothiazepine derivative, or a salt thereof, of formula 1

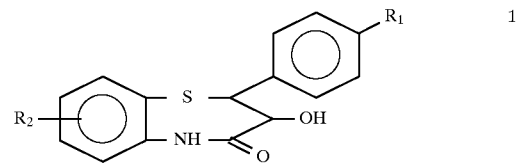

where R1 represents H, an alkyl group or an alkoxy group and $R_2$ represents H or a halogen, in which process a propanoic acid derivative of formula 2

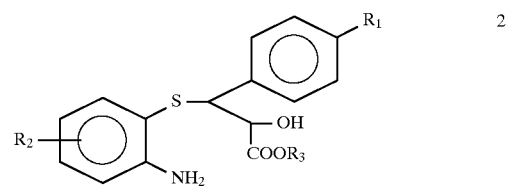

where $R_1$ and $R_2$ are as defined above and $R_3$ represents H or an alkyl group is subjected to an intramolecular cyclisation reaction in a non-halogenated solvent in the presence of a carboxylic acid. Preferably, $R_2$ is H and $R_1$ is $OCH_3$. Trichloroacetic acid is preferably used as α-chlorinated acid. The benzothiazepine obtained on cyclisation can be subjected to an alkylation reaction and/or an acylation reaction to obtain known pharmaceutical products, in particular diltiazem.

15 Claims, No Drawings

PROCESS FOR THE PREPARATION OF A BENZOTHIAZEPINE

BACKGROUND OF THE INVENTION

1. Field of the Invention

The invention relates to a process for the preparation of a 1,5-benzothiazepine derivative, or a salt thereof, of formula 1

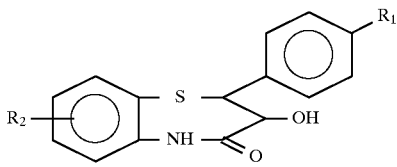

where $R_1$ represents H, an alkyl group or an alkoxy group and $R_2$ represents H or a halogen, in which process a propanoic acid derivative of formula 2

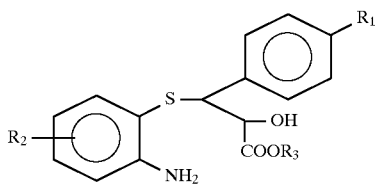

where $R_1$ and $R_2$ are as defined above and $R_3$ represents H or an alkyl group, is subjected to an intramolecular cyclisation reaction in a non-halogenated solvent in the presence of a carboxylic acid.

2. Description of Related Art

A process of the same kind is known from Chem. Pharm. Bull. 19, 2028–2037 (1970), in which inter alia acetic acid is mentioned as catalyst in the cyclisation of such propanoic acid derivatives.

A drawback of the known process is that the yield is very low, even at relatively long reaction times.

SUMMARY OF THE INVENTION

The present invention is directed to a process for the preparation of a 1,5-benzothiazepine derivative, or a salt thereof, of formula 1

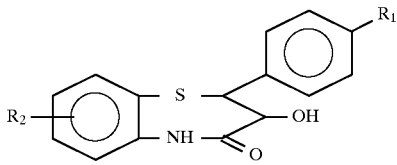

where $R_1$ represents H, an alkyl group or an alkoxy group and $R_2$ represents H or a halogen, in which process a propanoic acid derivative of formula 2

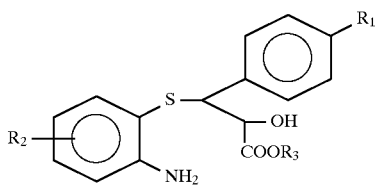

where $R_1$ and $R_2$ are as defined above and $R_3$ represents H or an alkyl group is subjected to an intramolecular cyclisation reaction in a non-halogenated solvent in the presence of a carboxylic acid, characterized in that an α-chlorinated carboxylic acid is used as carboxylic acid.

DETAILED DESCRIPTION OF THE INVENTION

The invention aims to provide a process enabling the cyclisation of the aforementioned propanoic acid derivatives in a short time and with a high yield.

This is accomplished according to the invention by applying an α-chlorinated carboxylic acid as carboxylic acid.

Examples of suitable α-chlorinated carboxylic acids are acids of the general formula R—C(Cl)$_n$—COOH, where R represents Cl, an alkyl group or an aryl group and n may be 1 or 2. The number of C atoms contained in R is not critical and in practice preferably is between 0 and 20, in particular between 0 and 3. Preferably, n equals 2. The best results are obtained using trichloroacetic acid.

The amount of α-chlorinated carboxylic acid to be applied usually is between 0.1 and 100 mole % of α-chlorinated carboxylic acid, calculated in relation to the amount of propanoic acid derivative used. When the acid of propanoic acid derivative is used as starting material for the cyclisation reaction, it is preferred to use 0.1–10 mole %, in particular between 2 and 6 mole % of α-chlorinated carboxylic acid, calculated in relation to the amount of propanoic acid derivative; when an ester is used as propanoic acid derivative it is preferred to use 10–80 mole %, in particular between 20 and 60 mole % of α-chlorinated carboxylic acid, calculated in relation to the amount of propanoic acid derivative.

Suitable starting compounds are propanoic acid derivatives of formula 2, where $R_1$ represents H, an alkyl group or an alkoxy group, in particular an alkyl group or an alkoxy group containing 1–20 C atoms, preferably 1–5 C atoms; $R_2$ represents H or a halogen, in particular Cl, and $R_3$ represents H or an alkyl group, in particular an alkyl group containing 1–20 C atoms, preferably 1–5 C atoms.

The choice of non-halogenated solvent applied in the process of the invention is not particularly critical. Examples of suitable solvents are hydrocarbons, in particular aromatic hydrocarbons, for example benzene, xylene, toluene or aliphatic hydrocarbons, for example n-hexane, n-heptane, n-octane or cyclohexane; or ethers, for example propylether. Preferably, xylene or toluene is used.

The temperature at which cyclisation according to the invention is carried out is not particularly critical either. In practice, the temperature preferably is between 50° and 200° C., in particular between 100° and 170° C.

The propanoic acid derivatives to be used as starting material can be prepared in a manner known in the art, for example by linking aminothiophenol with the corresponding derivative of phenylglycidic acid. If desired, the linking reaction to form the propanoic acid derivative and the subsequent cyclisation of the propanoic acid derivative can be carried out without isolating the propanoic acid derivative in the interim.

Subsequently, the 1,5 benzothiazepine obtained can be converted into known pharmaceutical compounds, for example diltiazem, in a manner known in the art, for example alkylation and acylation. Diltiazem is the name commonly used for (+)-(2S,3S)-2-(4-methoxyphenyl)-3-acetyloxy-5-[2-(dimethylamino)ethyl]-2,3-dihydro-1,5-benzothiazepin-4(5H)-one and is disclosed in for example U.S. Pat. No. 3,562,257.

The invention is now illustrated by the examples without being limited thereto.

EXAMPLES

Example I

Cyclisation of (+)-(2S,3S)-2-hydroxy-3-(4-methoxyphenyl)-3-(2-aminophenylthio)propanoic acid methyl ester with trichloroacetic acid.

820 mg of trichloroacetic acid was added to a solution of 3.3 grammes of (+)-(2S,3S)-2-hydroxy-3-(4-methoxyphenyl)-3-(2aminophenylthio)propanoic acid methyl ester in 30 ml of o-xylene under a nitrogen atmosphere at 90° C. Subsequently, the solution was heated on to the reflux temperature. The methanol formed was removed by azeotropic distillation. After one hour the solution was cooled to 15° C. and stirring was continued at this temperature for one hour. The precipitate formed was filtered off and washed first with o-xylene and then with iced water. After drying, the yield of (+)-(2S,3S)-2-(4-methoxyphenyl)-3-hydroxy-2,3dihydro-1,5-benzothiazepin-4(5H)-one was 2.4 g (81%).
purity: >98% ($^1$H-NMR)
melting point=203° C. $[\alpha]_D^{20}$=+115° C. (c=0,4; MeOH).

Example II

Cyclisation of (+)-(2S,3S)-2-hydroxy-3-(4-methoxyphenyl)-3-(2-aminophenylthio)propanoic acid methyl ester with trichloroacetic acid.

320 mg of trichloroacetic acid was added to a solution of 3.3 grammes of (+)-(2S,3S)-2-hydroxy-3-(4-methoxyphenyl)-3-(2-aminophenylthio)propanoic acid methyl ester in 30 ml of o-xylene under a nitrogen atmosphere at 90° C. Subsequently, the solution was heated on to the reflux temperature. The methanol formed was removed by azeotropic distillation. After one hour a second amount of 320 mg of trichloroacetic acid was added. After a total reaction time of two hours the solution was cooled to 15° C. and stirring was continued at this temperature for one hour. The precipitate formed was filtered off and washed first with o-xylene and then with iced water. After drying, the yield of (+)-(2S,3S)-2-(4-methoxyphenyl)-3-hydroxy-2,3-dihydro-1,5-benzothiazepin-4(5H)-one was 2.5 g (84%).
purity: >98% ($^1$H-NMR)

Example III

Cyclisation of (+)-(2S,3S)-2-hydroxy-3-(4-methoxyphenyl)-3-(2-aminophenylthio)propanoic acid methyl ester with 2,2-dichlorooctadecanoic acid. 177 mg of 2,2-dichlorooctadecanoic acid was added to a solution of 3,3 grammes of (+)-(2S,3S)-2-hydroxy-3-(4-methoxyphenyl)-3-(2-aminophenylthio)propanoic acid methyl ester in 30 ml of o-xylene under a nitrogen atmosphere at 90° C. Subsequently, the solution was heated on to the reflux temperature. The methanol formed was removed by azeotropic distillation. After one hour, a second amount of 177 mg of 2,2-dichlororoctadecanoic acid was added. A third amount of 707 mg of 2,2-dichlorooctadecanoic acid was added again after one hour. After a total reaction time of 3 hours the solution was cooled to 15° C. and stirring was continued at this temperature for one hour. The precipitate formed was filtered off and washed first with o-xylene and then with iced water. After drying, the yield of (+)-(2S,3S) -2-(4-methoxyphenyl)-3-hydroxy-2,3-dihydro-1,5-benzothiazepin-4(5H)-one was 2.2g (73%).
purity: >98% ($^1$H-NMR)

Example IV

Cyclisation of (+)-(2S,3S)-2-hydroxy-3-(4-methoxyphenyl)-3-(2-aminophenylthio)propanoic acid with trichloroacetic acid.

34 mg of trichloroacetic acid was added to a solution of 1.36 grammes of (+)-(2S,3S)-2-hydroxy-3-(4-methoxyphenyl)-3-(2-amino-phenylthio)propanoic acid in 20 ml of o-xylene under a nitrogen atmosphere at 110° C. Subsequently, the solution was heated on to the reflux temperature. The water formed was removed through azeotropic distillation. After two hours the solution was cooled to 15° C. and stirring was continued at this temperature for one hour. The precipitate formed was filtered off and washed first with o-xylene and then with iced water. After drying, the yield of (+)-(2S,3S)-2-(4-methoxyphenyl)-3-hydroxy-2,3-dihydro-1,5-benzothiazepin-4(5H)-one was 1,01 g (81%).
purity: >98% ($^1$H-NMR).

Example V

Synthesis of (+)-(2S,3S)-2-(4-methoxyphenyl)-3-hydroxy-2,3-dihydro-1,5-benzothiazepin-4(5H)-one from (2R,3S)-2,3-epoxy-3-(4-methoxyphenyl)propanoic acid methyl ester.

A solution of 10.4 grammes of (2R,3S)-2,3-epoxy-3-(4-methoxyphenyl)propanoic acid methyl ester and 150 μl triethylamine was heated under a nitrogen atmosphere to 120° C. At this temperature, 6.9 grammes of 2-aminothiophenol was added drop-wise in 30 minutes. 2.05 grammes of trichloroacetic acid was added after stirring for 1.5 hours at 120° C. The methanol formed was removed by azeotropic distillation. After one hour a second amount of 2.05 grammes of trichloroacetic acid was added. After a total reaction time of 2 hours the solution was cooled to 15° C. and stirring was continued at this temperature for one hour. The precipitate formed was filtered off and washed first with o-xylene and then with iced water. After drying, the yield of (+)-(2S,3S)-2-(4-methoxyphenyl)-3-hydroxy-2,3-dihydro-1,5-benzothiazepin-4(5H)-one was 10.6 g (71%).
purity: >98% ($^1$H-NMR)

We claim:

1. A process for the preparation of a 1,5-benzothiazepine derivative, or a salt thereof, represented by the formula 1

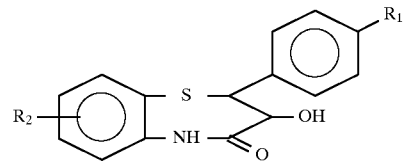

where $R_1$ represents H, an alkyl group or an alkoxy group and $R_2$ represents H or a halogen, in which process a propanoic acid derivative represented by the formula 2

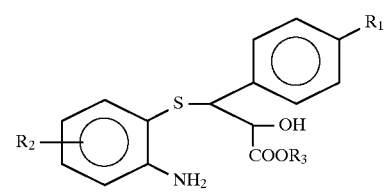

where $R_1$ and $R_2$ are defined above and $R_3$ represents H or an alkyl group is subjected to an intramolecular cyclisation reaction in a non-halogenated solvent in the presence of a carboxylic acid, wherein the carboxylic acid comprises an α-chlorinated carboxylic acid.

2. The process of claim 1 in which the amount of halogenated carboxylic acid is between 0.1 and 100 mole % (α-chlorinated carboxylic acid, calculated in relation to the amount of propanoic acid derivative having the formula 2.

3. The process of claim 1 or 2, in which $R_2$ is H and $R_1$ is $OCH_3$.

4. The process of claim 1 wherein said carboxylic acid has at least 2 Cl substituents on the α-site.

5. The process of claim 4 wherein said α-chlorinated carboxylic acid is trichloroacetic acid.

6. The process of claim 1 in which $R_3$ is H.

7. The process of claim 6 in which the amount of α-chlorinated carboxylic acid is between 2–6 mole %, calculated in relation to the amount of propanoic acid derivative having the formula 2.

8. The process of claim 1 in which $R_3$ represents an alkyl group.

9. The process of claim 8 in which $R_3$ represents an alkyl group having 1–5 C atoms.

10. The process of claim 8 or 9 in which the amount of α-chlorinated carboxylic acid is between 20 and 60 mole %, calculated in relation to the amount of propanoic acid derivative of the formula 2.

11. The process of claim 1, wherein said solvent is o-xylene.

12. The process of claim 1, further comprising subjecting the benzothiazepine obtained by cyclisation to an alkylation reaction so as to obtain a 2-dimethylaminoalkyl group attached to the nitrogen atom in the 5-position of the benzothiazepine ring and to an acylation reaction so as to obtain an acetyloxy group attached to the C-atom in the 3-position of the benzothiazepine ring.

13. The process of claim 12 in which diltiazem is prepared.

14. The process of claim 5, in which $R_3$ is H.

15. The process of claim 14, in which the amount of α-chlorinated carboxylic acid is between 2–6 mole %, calculated in relation to the amount of propanoic acid derivative having the formula 2.

* * * * *